Figure 5B:
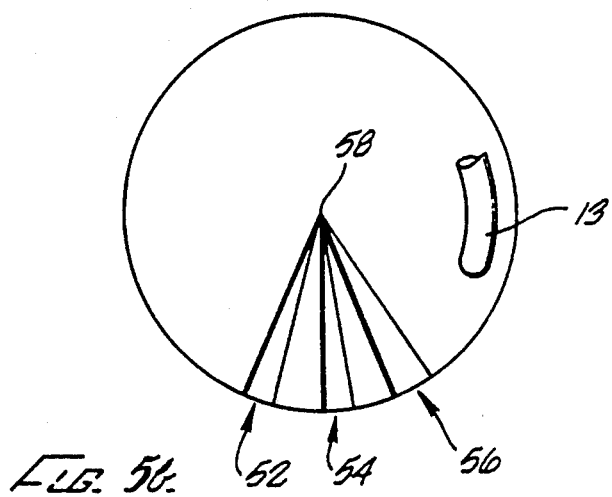

United States Patent [19]
Neward

[11] Patent Number: 5,222,498
[45] Date of Patent: Jun. 29, 1993

[54] SPIRAL ELECTRODE WITH CONTACT RETAINER

[76] Inventor: Theodore C. Neward, P.O. Box 725, Cucamonga, Calif. 91730

[21] Appl. No.: 924,159

[22] Filed: Aug. 3, 1992

Related U.S. Application Data

[63] Continuation-in-part of Ser. No. 654,268, Feb. 11, 1991, Pat. No. 5,150,709.

[51] Int. Cl.$^5$ .......................................... A61B 5/0408
[52] U.S. Cl. .................................... 128/642; 128/698
[58] Field of Search ............................... 128/642, 698

[56] References Cited

U.S. PATENT DOCUMENTS

| | | | |
|---|---|---|---|
| Re. 28,990 | 10/1976 | Hon et al. | 128/642 |
| 3,750,650 | 8/1973 | Ruttgers | 128/642 |
| 4,355,642 | 10/1982 | Alferness | 128/642 |
| 4,658,825 | 4/1987 | Hochberg et al. | 128/642 X |
| 4,913,151 | 4/1990 | Harui et al. | 128/642 X |

Primary Examiner—Lee S. Cohen
Assistant Examiner—Jeffrey R. Jastrzab
Attorney, Agent, or Firm—Lyon & Lyon

[57] ABSTRACT

A bipolar fetal monitoring electrode having an electrode body, a spiral electrode terminating in a point for engaging with fetal scalp, and a reference electrode insulated from the spiral electrode. The end of the electrode from which the spiral extends includes one or more protrusions in the form of points, ramps, ribs or the like to increase the resistance of the spiral from unwinding from the fetal scalp to which it is attached and thus to help prevent the spiral from unwinding spontaneously.

6 Claims, 3 Drawing Sheets

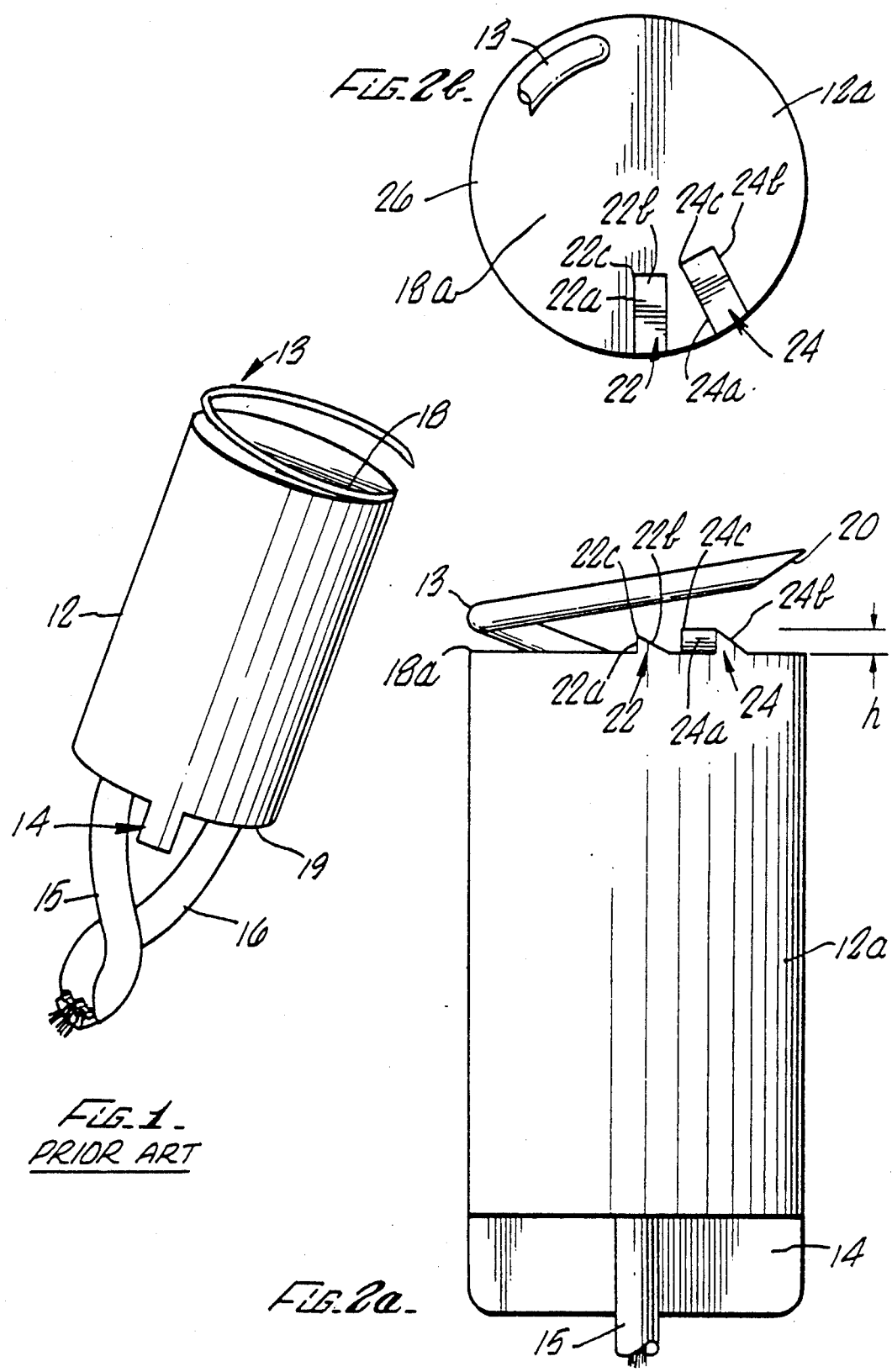

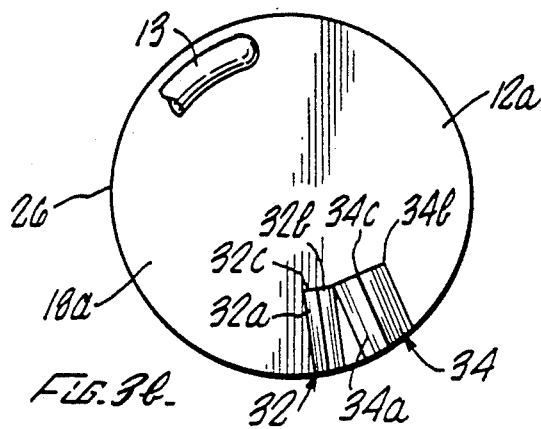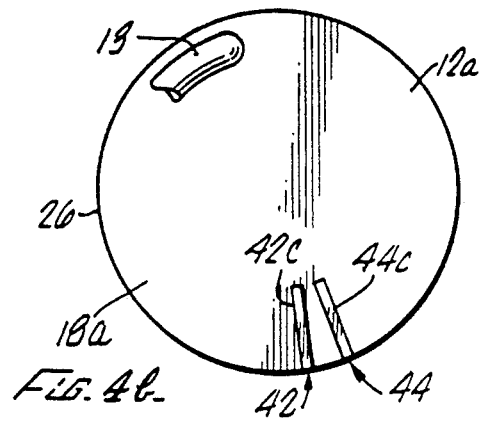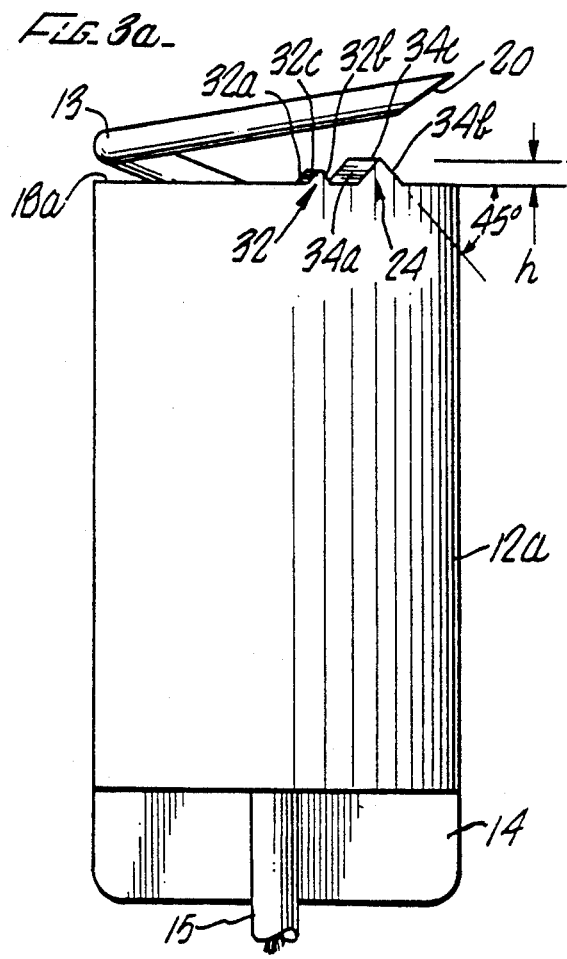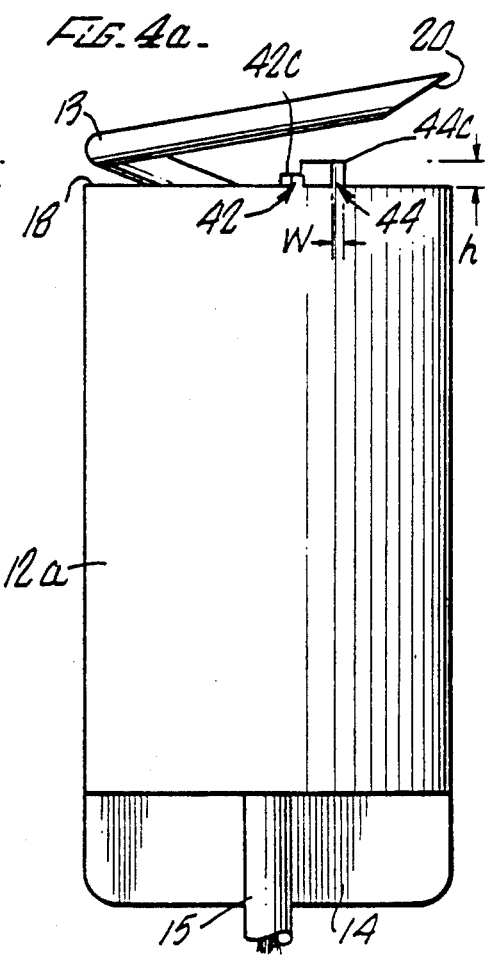

SPIRAL ELECTRODE WITH CONTACT RETAINER

This is a continuation-in-part of U.S. patent application Ser. No. 07/654,268, filed Feb. 11, 1991 now U.S. Pat. No. 5,150,709.

BACKGROUND

The present invention relates to a bipolar electrode structure particularly suitable for use in fetal heart monitoring.

Various forms of monitoring electrode structures have been developed. These include, for example, a body organ electrode shown in U.S. Pat. No. 3,416,534 which is arranged for insertion into the body through a hypodermic needle and to function as a pacemaker electrode, and a similar type shown in U.S. Pat. No. 3,472,234. Both of these electrodes have a spiral configuration for attachment to a body organ. Other examples are the implantable electrode shown in U.S. Pat. No. 3,737,579, and the double spiral fetal electrode shown in U.S. Pat. No. 3,750,650.

A type of electrode to which the present invention is particularly directed is shown in greater detail in applicant's U.S. Pat. No. 3,890,420 and U.S. Pat. No. 3,910,271, and in FIGS. 8-10 of Hon U.S. Pat. No. Re. 28,990. FIG. 1 of the present application illustrates this form of prior art electrode which comprises a bipolar electrode formed by injection molding to form a body 12 having a first spiral electrode 13 at the forward end thereof and a second wafer electrode 14 at the rear end thereof. The first and second electrodes 13 and 14 are made of a conductive metal such as stainless steel or the like, and each is respectively connected to first and second insulated wire conductors 15 and 16. The exposed surface of the wafer electrode 14 generally is approximately twice the exposed surface area of the electrode 13. The other ends of the conductors 15 and 16 are connected in a manner well known in the art to electronic monitoring equipment (not shown) suitable for monitoring fetal heartbeat, heart rate or the like. U.S. Pat. No. 3,890,420 discloses a method and molding apparatus for forming the electrode structure of FIG. 1.

The spiral electrode of the type shown in FIG. 1 has been widely accepted and has overcome the various problems of the "forceps-endoscope" and the "sliding sleeve-clip" type of electrodes, both of which include clips but which must be squeezed onto the fetal epidermis. The spiral electrode of FIG. 1, on the other hand, can be readily easily inserted through the vagina and cervix of a woman in labor or about to be in labor by suitable applying devices of the nature shown in U.S. Pat. No. 3,910,271 and U.S. Pat. No. Re. 28,990 and, thus, in many instances can be quickly and effectively applied to the fetus during an early stage of labor, and which can be quickly and easily removed.

However, it has been found through years of use of the form of spiral electrode of the type shown in FIG. 1 that the doctor will apply one electrode by screwing into the fetal epidermis, but in many instances it comes off and a second one (and sometimes even more) must be applied. It generally is too cumbersome to attempt to reapply a first electrode which has become detached and, thus, that electrode usually is removed and another electrode applied. Because of the nature of the spiral, and the "lead" or angle of the spiral 13, there is a tendency for the spiral to unwind or unscrew itself spontaneously or inadvertently from the fetal scalp after being connected to the fetal scalp by the doctor. This not only necessitates one or more additional electrodes to be tried, but also results in undue trauma to the fetal scalp.

The present invention involves a modification of a portion of the spiral electrode of the type shown in FIG. 1 so as to provide improved frictional contact between a surface of the electrode and the fetal skin to thereby minimize the opportunity for the spiral to unwind itself. According to exemplary embodiments of the present invention, the surface of the spiral electrode which is to contact the fetal scalp is provided with protrusions in the form of, for example, points, ribs, ramps or the like to cause added friction or interference, or to gather scalp, so as to reduce or minimize the possibility for the spiral to unwind or unscrew spontaneously or inadvertently from the scalp.

Accordingly, it is a principal object of the present invention to provide an improved form of spiral electrode.

Another object of this invention is to provide a spiral electrode wherein the end that contacts skin is modified to increase the friction or interference between the electrode and the skin so as to minimize loosening or unwinding of the electrode from the skin.

A further object of this invention is to provide a new form of fetal monitoring spiral electrode having protrusions in the form of, for example, a plurality of points, ramps, ribs or the like, molded in the surface of the electrode which contacts the skin so as to minimize inadvertent detachment of the electrode from the skin.

Another object of this invention is to provide a fetal monitoring spiral electrode which utilizes the spring action of the spiral to help hold the skin against the protrusions.

These and other objects and advantages of the present invention will become better understood through a consideration of the following description, taken in conjunction with the drawings in which:

IN THE DRAWINGS

Figure 5A:
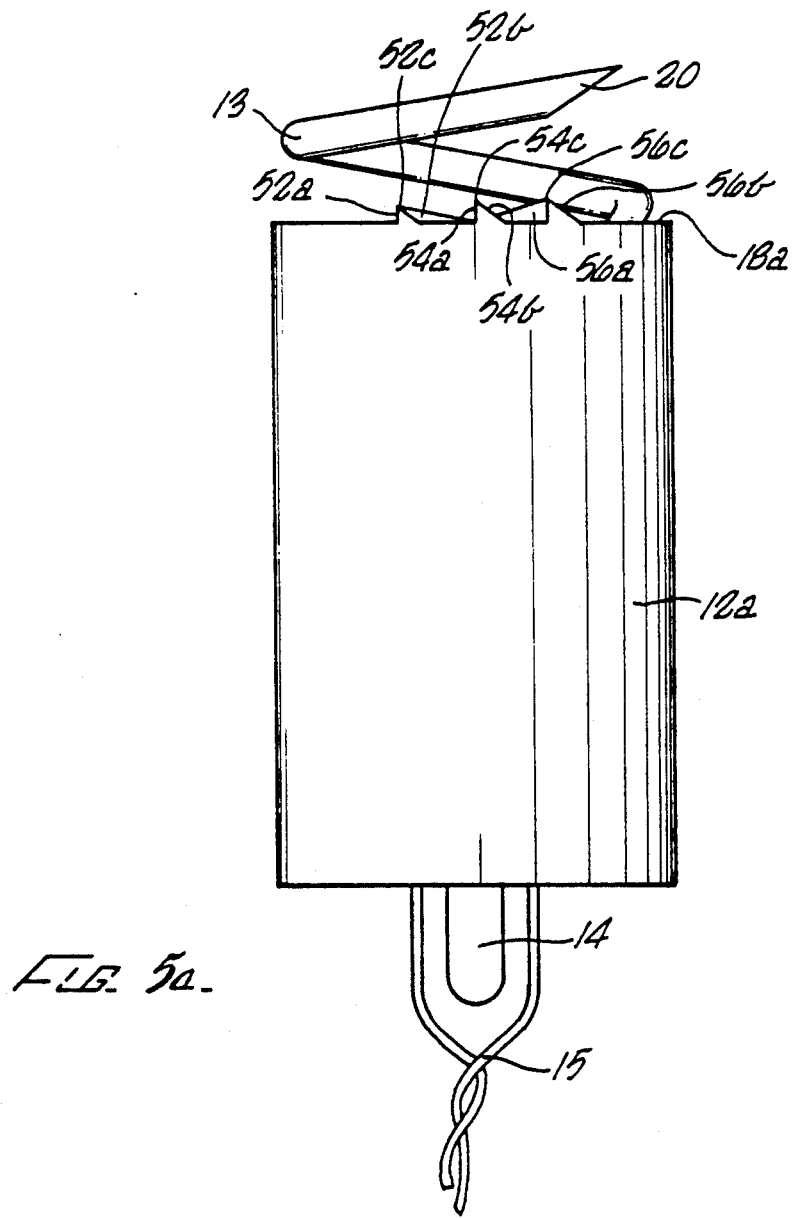

FIG. 1 is a perspective view of a conventional prior art fetal monitoring spiral electrode;

FIG. 2a is a side elevational view and FIG. 2b is a partial top plan view of a first embodiment of a modified spiral electrode according to the present invention including protrusions in the form of points molded as part of the electrode, FIG. 3a is a side elevational view and FIG. 3b is a partial top plan view illustrating another embodiment with protrusions in the form of points molded as part of the electrode, FIG. 4a is a side elevational view and FIG. 4b is a partial plan view of a third embodiment of an electrode having protrusions in the form of thin ribs molded as part of the electrode, and FIG. 5a is a side elevational view and FIG. 5b is a partial plan view of a fourth embodiment of an electrode having three protrusions extending from the center of the electrode.

Turning now to the drawings, and again to the prior art electrode in FIG. 1, the spiral 13 and wafer 14 electrodes are molded into the electrode body 12 as previously discussed and as more fully described in, for example, U.S. Pat. No. 3,890,420. The electrode of FIG. 1 includes the cylindrical plastic body 12 which has a first, proximal end 18 and a second, distal end 19. The spiral 13 of the electrode is pointed at 20 and when it is screwed into the fetal scalp, the first end 18 of the body 12 normally, at least initially, is adjacent the skin, and the second end 19 is disposed away from the fetal scalp. Because of the "lead" or angle (like screw threads) of the spiral 13 as noted earlier, there is a tendency for the electrode to unwind or unscrew spontaneously from the fetal scalp.

Turning now to the exemplary embodiments shown in FIGS. 2-4, like parts bear like or similar reference numerals to those in FIG. 1. Thus, in each of FIGS. 2 through 4 an injection molded electrode body is illustrated at 12a, and a spiral electrode 13, a wafer electrode 14, and one of the electrical conductors 15 are all shown (the spiral 13 is partially omitted from FIGS. 2b, 3b, 4b and 5b for clarity). A different reference numeral 12a is used for the plastic body of the electrode because a first, distal end 18a thereof is modified according to the present invention from the conventional electrode of FIG. 1. In each instance, the first surface 18a which confronts the skin of the fetus is modified in a manner to increase the friction or resistance, or to provide fetal skin gathering ability, so as to prevent or minimize spontaneous unwinding of the spiral 13 from the fetal skin.

In the arrangement shown in FIGS. 2a-2b, first and second protrusions in the form of right angle points 22 and 24 are provided. These preferably are molded into the body 12a during molding of the electrode. The points 22 and 24 are basically right angle triangular in shape, with first surfaces 22a and 24a essentially parallel to the longitudinal axis of the electrode, and second surfaces 22b and 24b being inclined downwardly toward the surface 18a from the respective apex 22c and 24c of the points. The heights of the points 22 and 24 typically may range from approximately 0.015 to 0.020 inch as illustrated in FIG. 2a, with 22 being shorter than 24 so as to maintain about an equal distance between the apexes 22c and 24c of these points and the spiral 13 (see FIG. 2a). Thus, the height difference of the points essentially is varied as the angle of the spiral 13. The points 22 and 24 may extend from the outer periphery 26 (note FIG. 2b) from underneath the spiral 13 radially inwardly partially toward the center of the surface 18a as best seen in FIG. 2b.

These points 22 and 24 molded as part of the electrode with one straight side (22a, 24a) serve to minimize the opportunity for the spiral to spontaneously unwind itself. However, the spiral can be readily easily removed from the fetal scalp by slightly pulling the electrode away from the scalp and unwinding the electrode. The points 22 and 24 thus act as an impediment to unscrewing the electrode from the fetal scalp by essentially digging into the flexible scalp or serving to gather the skin between points to thereby increase the friction between the surface 18a and the scalp.

The embodiment shown in FIGS. 3a-3b is similar to that shown in FIGS. 2a-2b, but in this case, protrusions in the form of points 32 and 34 are essentially in the form of forty-five degree triangles (when viewed from the periphery of the electrode as seen in FIG. 3a, thereby forming inclined sides (32a, 34a, and 32b, 34b) having an included angle of forty-five degrees extending to respective apexes 32c and 34c. As in the embodiment of FIG. 2, the points 32 and 34 can extend from the periphery 26 of the electrode body 12a from underneath the spiral 13 radially toward the center on the surface 18a as best seen in FIG. 3b. The points 32 and 34 help to gather the scalp between these points so as to minimize the opportunity for the spiral to unwind spontaneously. A typical height for the ribs 32 and 34 ranges from 0.010 to 0.015 inch as shown in FIG. 3a, with the rib 32 being the shorter and rib 34 being the taller.

Turning now to the embodiment of FIGS. 4a-4b, the same illustrates a pair of relatively thin ribs 42 and 44. In this embodiment, these ribs are rectangular as shown in FIG. 4 and extend radially from the periphery 26 toward the center of the surface 18a. The tops 42c and 44c can be flat as shown and substantially parallel to the surface 18a. A typical thickness for these ribs is approximately 0.010 inch wide, with the height of the two ribs 42 and 44 varying from approximately 0.010 to 0.015 inch as shown in FIG. 4a. These thin ribs 42 and 44 cause interference to help keep the spiral from unwinding spontaneously. These ribs can be slightly flexible so as to bend and help to lock the scalp between the wire spiral 13 and the surface or base 18a.

Turning now to the embodiment of FIGS. 5a-5b, the same illustrates a preferred embodiment with three ribs or protrusions 52, 54 and 56. In this embodiment, the three ribs are generally right angle triangular in shape, with first surfaces 52a, 54a and 56a essentially parallel to the longitudinal axis of the electrode, and second surfaces 52b, 54b and 56b inclined downwardly toward the surface 18a from the respective apex 52b, 54b and 56b of the points. Point 56c is higher off of surface 18a than point 54c, and point 54c is higher off of surface 18a than point 52c. Thus, the height difference of the points is varied as the angle of the spiral 13. The ribs 52, 54 and 56 extend radially inwardly from underneath the spiral 13 to the center 58 of the electrode body 12a where they meet. The angle between rib 52 and rib 54 is approximately equal to the angle between rib 54 and rib 56. The electrode 13 emerges from the electrode body 12a at a position adjacent to the rib 56.

As the spiral penetrates the skin during application of the electrode to the fetal scalp, the skin slides past the protrusions. When the physician stops rotating the spiral, the memory of the spiral pulls it down and pinches the skin against the protrusions. A different number of protrusions can be used.

The protrusions, such as the points and ribs as shown in FIGS. 2 through 5, thus help to increase the friction or interference between the electrode body 12a and the fetal skin either through their "roughness" to increase friction or interference, or through gathering fetal skin between the points or ribs, and along with the slight resilience of the spiral 13 to thus help minimize unwinding of the spiral 13. Stated differently, the spring or resilient action of the spiral 13, which is directly above the protrusions (or the latter are directly below the spiral depending on the point of reference), and the protrusions help to hold the skin against the protrusions. On the other hand, the electrodes still can be easily removed when necessary by pulling slightly on the conductors (e.g., 15 and 16) in a direction away from the fetal scalp (toward the bottom of the drawings in FIGS. 2a, 3a, 4a and 5a) which helps pull the protrusions away from the skin because of the resilience of the spiral 13. Because of this action, including the slight flexibility of the spiral 13, the interference or resistance is reduced to thereby allow the spiral 13 to be unscrewed upon demand (e.g., after delivery) in a manner already well familiar to physicians.

While specific exemplary embodiments of configurations of points, ramps, ribs and the like have been shown and discussed, it will be apparent to those skilled in the art that the shapes, numbers, widths, lengths, and the like of these protrusions from the base or surface 18a of the electrode can be modified in shape, number and the like, the important aspect of the invention being that the base or surface 18a is modified or roughened in a manner to engage the fetal scalp and increase the resistance to spontaneous unwinding of the spiral from the scalp.

While embodiments of the present invention have been shown and described, various modifications may be made without departing from the scope of the present invention, and all such modifications and equivalents are intended to be covered.

What is claimed is:

1. An electrode structure for use in fetal heart monitoring comprising:
   a substantially cylindrical electrode body formed of electrically insulating material and having a first end and a second end, a center and a perimeter edge,
   a spiral electrode extending from the first end of the electrode body and terminating in a pointed end adapted to pierce a fetal epidermal layer,
   a second electrode extending from the electrode body, said second electrode being spaced from and electrically insulated from the spiral electrode, and
   the first end of the electrode body having first, second and third protrusions of progressively increasing height directly underlying a portion of the spiral electrode and extending radially outwardly substantially from the center to the perimeter edge of the electrode body, to increase the resistance of the electrode structure from unwinding from the fetal epidermal layer.

2. The electrode structure of claim 1 wherein the spiral electrode extends from the first end of the electrode body adjacent the third protrusion.

3. An electrode structure for use in fetal heart monitoring comprising:
   a substantially cylindrical electrode body formed of electrically insulating material and having a first end and a second end, a center and a perimeter edge,
   a spiral electrode extending from the first end of the electrode body and terminating in a pointed end adapted to pierce a fetal epidermal layer,
   a second electrode extending from the electrode body, said second electrode being spaced from and electrically insulated from the spiral electrode, and
   the first end of the electrode body having first, second and third protrusions of progressively increasing height extending radially outwardly substantially from the center to the perimeter edge of the electrode body with radially outwardly portions of at least one of the protrusions directly underlying a portion of the spiral electrode, to increase the resistance of the electrode structure from unwinding from the fetal epidermal layer.

4. The electrode structure of claim 3 wherein the spiral electrode extends from the first end of the electrode body adjacent the third protrusion and a portion of the spiral electrode directly overlies each of the protrusions.

5. An electrode structure for use in fetal heart monitoring comprising:
   a substantially cylindrical electrode body formed of electrically insulating material and having a first end, and a center, and a perimeter edge
   a spiral electrode extending from the first end of the electrode body and terminating in a pointed end adapted to pierce a fetal epidermal layer,
   the first end of the electrode body having a plurality of protrusions of different heights extending radially outwardly substantially from the center to the perimeter edge of the electrode body and having outer portions directly underlying a portion of the spiral electrode, to increase the resistance of the electrode structure from unwinding from the fetal epidermal layer.

6. The electrode structure of claim 5 wherein there are three protrusions of progressively increasing height, and the spiral electrode extends from the first end of the electrode body adjacent and directly over the third protrusion.

* * * * *